(12) United States Patent
Shin et al.

(10) Patent No.: US 8,609,718 B2
(45) Date of Patent: Dec. 17, 2013

(54) PHARMACEUTICAL COMPOSITION USED IN TREATMENT OF HYPERPROLIFERATIVE SKIN CONDITIONS AND MALIGNANT MELANOMAS COMPRISING PACHASTRISSAMINE AS ACTIVE INGREDIENT

(75) Inventors: Dong Heon Shin, Seoul (KR); Tae Yoon Kim, Seoul (KR)

(73) Assignee: Catholic University Industry Academy Cooperation Foundation, Seoul (KR)

( * ) Notice: Subject to any disclaimer, the term of this patent is extended or adjusted under 35 U.S.C. 154(b) by 34 days.

(21) Appl. No.: 13/236,080

(22) Filed: Sep. 19, 2011

(65) Prior Publication Data

US 2012/0071424 A1    Mar. 22, 2012

Related U.S. Application Data (63) Continuation of application No. PCT/KR2010/001666, filed on Mar. 18, 2010.

(30) Foreign Application Priority Data

Mar. 18, 2009 (KR) .................. 10-2009-0023190

(51) Int. Cl.
*A61K 31/34* (2006.01)
(52) U.S. Cl.
USPC ........... 514/472; 514/859; 514/861; 514/863; 514/864
(58) Field of Classification Search
USPC ................. 514/472, 859, 861, 863, 864
See application file for complete search history.

(56) References Cited

PUBLICATIONS

Ladroit et al., "Jaspines A and B: two new cytotoxic sphingosine derivatives from the marine sponge Jaspis sp.", Tetrahedron Letters, vol. 44, No. 2, pp. 225-228 (2003).*
Canals, D. et al., "Synthesis and biological properties of Pachastrissamine (jaspine B) and diastereoisomeric jaspines," Bioorganic & Medicinal Chemistry, 17, pp. 235-241 (2009).
Kuroda, I. et al., "Pachastrissamine, a Cytotoxic Anhydrophytosphingosine from a Marine Sponge, Pachastrissa sp.," J. Nat. Prod., 65, pp. 1505-1506 (2002).
Liu, Jun, et al., "Stereoselective synthesis of jaspine B from D-xylose," Carbohydrate Research, 341, pp. 2653-2657 (2006).
Prasad, K. et al., "Stereoselective Synthesis of Cytotoxic Anhydrophytosphingosine Pachastrissamine [Jaspine B]," J. Org. Chem., 72, pp. 6312-6315 (2007).

* cited by examiner

*Primary Examiner* — Kevin E Weddington
(74) *Attorney, Agent, or Firm* — Edwards Wildman Palmer LLP (57) ABSTRACT

Disclosed is a novel use of phytosphingosine. More particularly, disclosed are a composition for preventing or treating hyper-proliferative skin diseases comprising pachastrissamine as an active ingredient, a use of pachastrissamine or a pharmaceutically acceptable salt thereof for preparing a preventing/therapeutic agent of hyper-proliferative skin diseases, and a method for treating hyper-proliferative skin diseases administering an effective amount of pachastrissamine or a pharmaceutically acceptable salt thereof to a subject in need thereof. The pachastrissamine inhibits the degradation of FoxO3a protein and increases the expression of FoxO3a protein. Thus, the inventive pharmaceutical composition has a preventing of treating effect on hyper-proliferative diseases by inducing apoptosis of hyper-proliferative cells and inhibiting the cell cycle. Accordingly, the disclosed composition, a use, and the method can be used for preventing or treating various hyper-proliferative skin diseases such as skin cancer or psoriasis.

2 Claims, 6 Drawing Sheets

PHARMACEUTICAL COMPOSITION USED IN TREATMENT OF HYPERPROLIFERATIVE SKIN CONDITIONS AND MALIGNANT MELANOMAS COMPRISING PACHASTRISSAMINE AS ACTIVE INGREDIENT

CROSS-REFERENCE TO RELATED APPLICATION

This application is a continuation of PCT/KR2010/001666 filed Mar. 18, 2010, which claims the benefit of Korean Application No. 10-2009-0023190 filed Mar. 18, 2009, the entire contents of which applications are incorporated herein by reference.

TECHNICAL FIELD

The present invention relates to a composition for preventing or treating hyper-proliferative skin diseases comprising pachastrissamine as an active ingredient, a use of pachastrissamine or a pharmaceutically acceptable salt thereof for preparing an agent for preventing or treating hyper-proliferative skin diseases, and a method for treating hyper-proliferative skin diseases comprising administering an effective amount of pachastrissamine or a pharmaceutically acceptable salt thereof to a subject in need thereof. More particularly, the present invention relates to a composition, an use, and a method for preventing and treating psoriasis and malignant melanoma through inhibition of a cell cycle and induction of apoptosis.

BACKGROUND ART

Continuous repetitions of a cell cycle maintain various functions of tissues while balancing the death and proliferation of cells. When the balance is broken, a disease is caused. In normal cell tissue, the number of tissue cells is regularly maintained due to the balance of the proliferation and death of cells. On the other hand, in tumorous cell tissue, since cell death is not properly carried out compared to rapid cell proliferation, the number of cells is greatly increased unlike the normal tissue and the cells become cancer cells (Raff. M. C., Nature, 356:397, 1992). Cell death is very important in the maintaining of such balance, and has two types of mechanisms. One is known as a conventional type of necrosis which is generally passively and accidentally caused. Morphologically, necrosis is characterized by causing a swelling of mitochondria and protoplasm, and nucleus damage, and then cells are led to death due to cytolysis and autolysis. For example, tissue necrosis is generally caused by physical injury or chemical toxicity of a cell. The other is apoptosis which is programmed cell death. Apoptosis is one type of cell death occurring in physiological and clinical conditions, and is closely related to a fetal development process, a tissue's growth, differentiation and homeostasis, and a cell's differentiation, growth, and maturation.

Sphingolipid is one type of membrane lipid which very importantly acts on the structural formation of a lipid bilayer. For the last 20 to 30 years, molecular-biological or biochemical researches on functions of sphingolipid and sphingolipid metabolite have been continued up to now. For such functions, researches on immunological or cell-biological functions through cell proliferation, apoptosis, cell migration, senescence have been conducted so far. However, specific results have been not yet achieved.

Skin is an organ which is positioned in the outermost layer of a human body, and is always exposed to an outer stimulus. Proliferative skin diseases are spread through the world, and millions of people and domesticated animals suffer from the diseases. The proliferative skin diseases are characterized by causing proliferation or differentiation of keratinocytes, and also may relate to imperfect epidermal differentiation. Psoriasis is the most serious disease in proliferative skin diseases related to the present invention.

Psoriasis is a hyper-proliferative skin disease of human skin, which is generally characterized by causing a macule covered with thickened squama (layered lump of keratin). Psoriasis is a representative intractable skin disease that is hardly completely healed, and its relapse and relief are repeated at intervals (Korean Dermatological Association, textbook compilation committee, $4^{th}$ revised edition, dermatology, Ch 12, papulosquamous disease, p 221, 2001). It is known that about 3% of Caucasians, about 2% of Native Americans, and about 1% of African-Americans suffer from psoriasis. Psoriasis is caused by hyper-proliferation of keratinocytes. Cells in normal skin reach a granulosa from a basal layer within about 4 weeks while cells with psoriasis rapidly proliferate and then reach the granulosa within only 6 to 9 days (Grove, G. L., Int. J. Dermatol., 18, 111-122, 1979). As described above, abnormal proliferation of cells is a cause of psoriasis, and thus the present treatment focuses on a delay of skin cell proliferation and a reduction of inflammation. Topical treatments for psoriasis may comprise a steroid cream treatment, an ultraviolet ray treatment (UVB, 290-320 nm), and a treatment using a vitamin D ointment for inhibiting the proliferation of skin cells. A steroid ointment is very effective but its therapeutic effect is not maintained for a long time. Thus, over the course of the application of a steroid ointment, its effect is reduced and side effects such as skin atrophy are caused. The ultraviolet ray treatment has a therapeutic effect which is maintained for a relatively long time, but causes troubles such as periodical hospital visits for treatments. Meanwhile, when the ultraviolet ray treatment is administered over too long a period of time, it may promote photoaging and increase the possibility of skin cancer. The vitamin D ointment does not cause the same side effects as the steroid ointment, but is effective in only 50% of patients treated by the steroid ointment. Further, it is known that the vitamin D ointment is very acrid. Psoriasis not only promotes angiogenesis but also rapidly proliferates keratinocytes. Accordingly, there have been suggested medicines for inducing apoptosis of such keratinocytes as effective therapeutic agents.

Malignant melanoma is the most dangerous cancer among various skin cancers, and is formed in a similar shape to a spot on a sole. In general, in frequent cases, people let the malignant melanoma go untreated without recognizing it as cancer, and in the end, they lose their lives. Among various skin cancers, a conspicuous symptom indicates that a cancer has already considerably progressed, and thus it is likely that the cancer spreads to other organs. However, metastasis of the malignant melanoma very strongly occurs, compared to those in other cancers. Thus, in many cases, people lose their lives by metastasized melanoma, not by malignant melanoma occurring in skin. Also, a cancer occurring in the skin has a considerably wide range, and thus a considerably wide area for an operation or a treatment is appointed so that the corresponding cancer region and its circumference can be scraped out or cut out. For this reason, patients may refuse treatment while seriously worsening a disease state. This repeatedly causes a vicious cycle. Besides these characteristics of the cancer, there are problems in that in general, people do not consider skin cancer as a serious disease, and let the disease go untreated, and many patients even refuse treatment. From 1980 to 2004, malignant melanoma incidences among young Caucasian women have risen by 50% per year. Also, the plastic surgery team of a national medical center carried out a retrospective analysis on 251 operation cases of skin cancer over 15 years from 1993 to 2007. As a result, in 50% of the cases, skin-cancer relapse patients secondarily relapsed into cancer again.

The above information disclosed in this Background section is only for enhancement of understanding of the background of the invention and therefore it may contain information that does not form the prior art that is already known in this country to a person of ordinary skill in the art.

SUMMARY OF THE DISCLOSURE

The inventors of the present invention researched physiological functions of pachastrissamine, and then discovered new functions such as inhibition of a disease (such as psoriasis) caused by hyper-proliferation of kerationocytes or a skin cancer (such as malignant melanoma). Then, they developed a pachastrissamine containing composition which can be used for preventing psoriasis or malignant melanoma and for carrying out pharmacotherapy (instead of an extreme remedy such as cut-out or incision) so as to complete the present invention.

Accordingly, one aspect of the present invention provides a pharmaceutical composition for preventing or treating hyper-proliferative skin diseases comprising pachastrissamine or a pharmaceutically acceptable salt thereof as an active ingredient.

Another aspect of the present invention provides a use of pachastrissamine or a pharmaceutically acceptable salt thereof for preparing an agent for preventing or treating hyper-proliferative skin diseases.

A further aspect of the present invention provides a method for treating hyper-proliferative skin diseases comprising administering an effective amount of pachastrissamine or a pharmaceutically acceptable salt to a subject in need thereof.

As described above, the inventive pharmaceutical composition for preventing or treating hyper-proliferative skin diseases comprises pachastrissamine or a pharmaceutically acceptable salt thereof as an active ingredient. The pachastrissamine inhibits the degradation of FoxO3a protein and increases the expression of FoxO3a protein. Thus, the inventive pharmaceutical composition induces apoptosis of hyper-proliferative cells and is effective in apoptosis in skin cancer such as malignant melanoma. Accordingly, the inventive pharmaceutical composition comprising pachastrissamine or a pharmaceutically acceptable salt thereof as an active ingredient can be used for preparing agents for treating and preventing hyper-proliferative skin diseases such as skin cancer, and psoriasis.

BRIEF DESCRIPTION OF THE DRAWINGS

The above and other objects, features and advantages of the present invention will be more apparent from the following detailed description taken in conjunction with the accompanying drawings, in which.

DETAILED DESCRIPTION OF THE DISCLOSURE

Reference will now be made in detail to the preferred embodiment of the present invention, examples of which are illustrated in the drawings attached hereinafter, wherein like reference numerals refer to like elements throughout. The embodiments are described below so as to explain the present invention by referring to the figures.

As described above, aspects of the present invention provides a pharmaceutical composition for preventing or treating hyper-proliferative skin diseases comprising pachastrissamine or a pharmaceutically acceptable salt thereof as an active ingredient, a use thereof, and a method for treating hyper-proliferative skin diseases comprising administering an effective amount of pachastrissamine or a pharmaceutically acceptable salt to a subject in need thereof.

The inventive pachastrissamine has a structure represented by Formula 1 below, and may be obtained through separation and purification from natural sources, commercially bought, or prepared by a chemical synthesis known in the art.

[Chemical Formula 1]

Pachastrissamine may be separated/purified from Pachastrissa of a marine sponge. The inventive pachastrissamine may be extracted by using an organic solvent (such as water, alcohol having 1 to 6 carbon atoms (e.g., ethanol and methanol), acetone, ethyl acetate, n-hexane, diethyl ether, acetone, benzene) or may be extracted by a technique conventionally used in the art (such as chromatography).

The present invention provides a pharmaceutical composition for preventing or treating hyper-proliferative skin diseases, which comprises pachastrissamine or a pharmaceutically acceptable salt thereof as an active ingredient. The inventive composition may comprise 0.001% to 99.999% of pachastrissamine or a pharmaceutically acceptable salt thereof, and the residual content of a carrier.

In the present invention, a hyper-proliferative skin disease indicates a disease caused by hyper-proliferation of skin cells constituting biological tissues due to the loss of proliferation controllability. Non-limiting examples of the disease may comprise skin cancer, ichthyosis, solar keratosis, Bowen's disease, papilloma, eczema, addictive eczema, atopic dermatitis, acne vulgaris, seborrheic dermatitis, lichen planus, lichen planus striatus, foot hyperkeratosis, seborrheic keratosis, actinic keratosis, cutaneous wart lesion, skin aging, photoaging and various types of psoriasis (such as psoriasis vulgaris and pustular psoriasis). More preferably, the disease may be psoriasis or malignant melanoma.

The inventive pachastrissamine's effect on prevention or treatment of diseases caused by cell hyper-proliferation was tested through experiments by the inventors.

In other words, in Example 1, in order to determine if the pharmaceutical composition has a cytotoxic effect on hyper-proliferated cells, a human keratinocyte cell line (HaCaT) and a malignant melanoma cell line (B16F10, A375) were cultured and the inventive pachastrissamine was added in various concentrations. Then, through MTT assay, the viability of cells was measured. As a result, as the concentration of pachastrissamine was increased, the number of surviving cells was reduced. Thus, it was determined that pachastrissamine has a cytotoxic effect on hyper-proliferated cells.

In Example 2-1, in order to precisely understand the mechanism of the cytotoxic effect of the inventive pachastrissamine, it was observed whether pachastrissamine has an effect on cell proliferation of hyper-proliferative cells or induces apoptosis. In order to determine if pachastrissamine inhibits cell proliferation, HaCaT cells were added with pachastrissamine, and cultured. Then, the number of cells was measured at time intervals, and was compared with that in a control group. As a result, the number of cells in the control group was increased over the course of a culturing time while the number of cells added with pachastrissamine was reduced over the course of a culturing time. Accordingly, it was found that pachastrissamine has an effect on the inhibition of cell proliferation of hyper-proliferative cells.

In Example 2-2, in order to determine the induction of apoptosis, one group where HaCaT cells and malignant melanoma cells were added with pachastrissamine and cultured, and another group where the cells were added with lithium chloride (apoptosis inhibiting material) as well as pachastrissamine and cultured were compared to each other through measurement of the number of cells. As a result, it was found that the group further added with lithium chloride showed a reduced effect on the reduction of the number of cells as compared to the group added with only pachastrissamine. Also, through a TUNEL method by using an apoptosis detection kit, the progress of apoptosis of each cell culture group was observed. As a result, when pachastrissamine was added, it was determined that apoptosis was progressed in most of the observed cell nucleuses.

In Example 3-1, in order to precisely understand the mechanism of pachastrissamine on the inhibition of cell proliferation of a HaCaT cell line and a malignant melanoma cell line, and the induction of apoptosis, pachastrissamine's effect on the control of the activity of AKT and the activity of ERK was researched. In order to determine the effect on the activity of AKT, the change of AKT protein was measured through western blotting, in a HaCaT cell line and a malignant melanoma cell line, added with pachastrissamine and cultured. In order to determine the effect on the activity of ERK, the change of ERK protein in a HaCaT cell line, added with pachastrissamine and cultured, was compared through western blotting with a group added with U0126 (ERK inhibitor) as well as pachastrissamine and a group added with only U0126.

As a result, it was found that after 30 minutes from treatment with pachastrissamine, the phosphorylation extent of AKT was decreased, and it was also found that after 60 minutes from treatment with pachastrissamine, the phosphorylation extent of AKT was increased.

The effect on the activity of ERK was analyzed. As a result, it was found that the addition of pachastrissamine almost completely inhibited the phosphorylation of ERK like the addition of U0126. Also, in a case where the phosphorylation of ERK was promoted by further treatment with EGF, it was found that pachastrissamine inhibited the phosphorylation of ERK. Also, in one case where phosphorylation of ERK was promoted through over-expression of caMEK (constitutively active MEK1 mutant), and in another case where MEK was activated through over-expression of Ras, the pachastrissamine's effect on activation inhibition of ERK or MEK was analyzed. As a result, it was found that pachastrissamine's effect on activation inhibition of ERK was caused by an inhibition effect on MEK as an upper signal (see Example 3-2).

In order to clarify the induction mechanism, the mechanism of pachastrissamine on the inhibition of cell proliferation of hyper-proliferative cells, and the induction of apoptosis, the pachastrissamine's effect on the expression regulation of FoxO3a (as a cell proliferation inhibitor) was analyzed. The amounts of FoxO3a protein and phosphorylated FoxO3a (pFoxO3a) protein in a cell line added/cultured with pachastrissamine were analyzed through western blotting. As a result, it was found that when pachastrissamine was added, the amounts of both proteins were increased (see Examples 4-1 and 4-2). Also, in order to determine if the mechanism of pachastrissamine on expression regulation of FoxO3a has a relation with AKT pathway, FoxO3a antibody and Alex488 (invitrogen) antibody as a secondary antibody were used to carry out immunocytochemistry. As a result, it was determined that the mechanism acted independently from AKT pathway (see Example 4-3).

In order to determine if the mechanism of pachastrissamine on expression regulation of FoxO3a has a relation with ERK pathway, a HaCaT cell line was added with U0126 and PD98059 (ERK inhibitors) together with pachastrissamine, or a HaCaT cell line was independently added with each of pachastrissamine, U0126 and PD98059, and then the amount of FoxO3a protein was measured through western blotting. As a result, it was found that when these materials were added unlike a negative control group, the amount of FoxO3a protein was increased. Also, it was found that when pachastrissamine was added together with U0126, the increase rate was further increased. In order to clarify the mechanism of ERK on the control of an amount of FoxO3a protein, EGF activating ERK was added together with pachastrissamine, and the cultured cells were subjected to cytolysis. Then, by using FoxO3a antibody, through immunoprecipitation, a sample was separated. Then, by using ubiquitin antibody, through western blotting, the ubiquitination degree of FoxO3a protein was measured. As a result, it was found that the ubiquitination degree increased by EGF was decreased by treatment with pachastrissamine. Accordingly, it was determined that the degradation of FoxO3a protein by ERK was inhibited by pachastrissamine (see Example 4-4).

In order to determine if beta-catenin participates in a process where pachastrissamine inhibits the activation (phosphorylation) of ERK and thus ERK's effect on the promotion of FoxO3a degradation is inhibited, a culture cell was added with each of pachastrissamine and lithium chloride (an inhibitor of GSK3-beta, GSK3-beta=beta-catenin inhibiting protein) and was subjected to cytolysis. Then, through western blotting, the amounts of pGSK3-beta, GSK3-beta, pCatenin and Catenin were measured. As a result, in a group added with lithium chloride, the phosphorylation of GSK3-beta was progressed, thereby inhibiting the protein activity. Then, the phosphorylation of beta-catenin was inhibited, stabilizing bete-catenin. On the other hand, in a case of pachastrissamine, phosphorylation of GSK3-beta was inhibited, thereby increasing the phosphorylation of beta-catenin (see Example 5-1).

In order to clarify beta-catenin's effect on FoxO3a protein degradation and pachastrissamine's effect on this process, in a HaCaT cell line with over-expression of beta-catenin and a negative control group, the amount of FoxO3a protein was measured through western blotting. As a result, it was found that in a cell line with an over-expression of beta-catenin, the expression of FoxO3a was decreased. Also, when the same cell group was treated with U0126 (ERK inhibitor), the expression of FoxO3a and beta-catenin was analyzed. In a case where ERK was inhibited, the expression of beta-catenin showed no change and the expression of FoxO3a was restored to a normal state. Accordingly, it was determined that degradation of FoxO3a by ubiquitin was inhibited through pachastrissamine's beta-catenin-dependent ERK phosphorylation inhibition (see Example 5-2).

The inventive pachastrissamine's effect on prevention or treatment of diseases caused by cell hyper-proliferation was testified through animal experiments by the inventors.

In other words, in Example 6, in order to determine if the pharmaceutical composition inhibits the metastasis of malignant melanoma in a mouse malignant melanoma metastasis model, a mouse (aged 6 weeks) was inoculated with a malignant melanoma cell line, and after 24 hours, for a predetermined period, pachastrissamine was inoculated. Then, the lung was extracted and was compared to that of a control group.

As a result, it was found that the mouse inoculated with pachastrissamine showed a significantly inhibited metastasis of malignant melanoma compared to the control group (see Example 6).

The pachastrissamine of the present invention may be used as it is or in the form of a pharmaceutically acceptable salt. As used herein, the phrase "pharmaceutically acceptable" means that the components present in the composition are physiologically acceptable and usually do not invoke allergic or similar reactions when administered to humans. Specifically, the salt may be an acid addition salt formed from a pharmaceutically acceptable free acid. The free acid may be an organic or inorganic acid. The organic acid comprises but is not limited to citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, glutamic acid and aspartic acid. And, the inorganic acid comprises but is not limited to hydrochloric acid, bromic acid, sulfuric acid and phosphoric acid.

A pharmaceutical composition of the present invention may comprise pachastrissamine or pharmaceutically acceptable salt thereof alone or further comprise pharmaceutically acceptable carriers, stabilizers, preservatives, exipients or diluents.

A pharmaceutically acceptable carrier, for example, carriers for the parenteral or oral preparations may be comprised. The carriers for the oral preparations may comprise lactose, starch, cellulose derivatives, magnsium stearate, stearic acid and the carriers for the parenteral preparations may comprise water, oil, saline, aqueous glucose and glycol. The examples of the stabilizers may be sodium hydrogen sulfite, sodium sulfite, and ascorbic acid. The examples of the preservatives may be benzalkonium chloride, methyl- or prophyl-paraben, and chlorobutanol. The list of pharmaceutically acceptable carriers are disclosed in Remington's Pharmaceutical Sciences, 19th ed., Mack Publishing Company, Easton, Pa., 1995.

The pharmaceutical composition of the present invention may be administered by any routes, for example, oral or parenteral routes. The parenteral routes comprise, not limited thereto, intravenous, intramuscular, intraarterial, intramarrow, intra pachymeninx, intracardiac, intradermal, subcutaneous, peritorial, intranasal, gastrointestinal tracts, sublingual or rectum. Preferably, the pharmaceutical composition of the present invention may be administered by dermal administration. The dermal administration refers that injecting a pharmaceutical composition of the present invention into cells or skin and delivering the active component of the pharmaceutical composition into the skin. For example, a pharmaceutical composition of the present invention may be formulated into an injection and administered by lightly pricking the skin with 30-gauge injection needle or by applying it onto skin directly.

A pharmaceutical composition of the present invention may be formulated into reagent for oral administration or parenteral administration according to the mentioned above.

In case of the formulation for oral administration, the composition of the present invention may be formulated with a proper carrier for oral administration into powders, granules, tablets, pills, and sugar-coated tablets, capsules, liquids, gels, syrups, slurries, and emulsions by using the method known in the art. For examples of appropriate carriers, it may comprise sugars comprising lactose, dextrose, sucrose, sorbitol, mannitol, xylitol, erythritol and maltitol, starches comprising corn starch, wheat starch, rice starch and potato starch, celluloses comprising cellulose, methyl cellulose, sodium carboxymethylcellulose and hydroxypropylmethylcellulose, and fillers comprising gelatin and polyvinylpyrrolidone. And, if desired, it may comprise cross-linked polyvinylpyrrolidone, agar, alginic acid or sodium alginate as a solutionizer. Further, the inventive pharmaceutical composition may comprise anti-coaglutinating agent, lubricant, wetting agents, flavors, emulsifying agents and antiseptics.

In case of parenteral preparations, it comprise ointments, injections, creams, lotions, ointments, oils, humectants, gels, aerosols and nasal inhalants according to the skills well known in the art.

Total effective amount of pachastrissamine of the present invention may be administered with single dose or multiple doses for long term. The pharmaceutically effective amount suitably determined by considering various factors, such as severity of disease, administration route, age of patient, body weight, health condition, sex, diet and excretion rate. The formulations, administration routes and administration methods of the present invention are not limited as long as it shows an effect of the present invention.

Meanwhile, the present invention provides a use of pachastrissamine or a pharmaceutically acceptable salt thereof for preparing a preventing/therapeutic agent of hyper-proliferative skin diseases. In addition, the present invention provides a method for treating hyper-proliferative skin diseases, in which pachastrissamine or a pharmaceutically acceptable salt thereof is administered in an effective dose to a subject in need.

As used herein, the "effective amount" refers to the amount of pachastrissamine effective in treating disease of a subject, and the "subject" refers to mammals, particularly, animals comprising human. The subject may be patient in need of treatment.

EXAMPLES

Hereinafter, the present invention will be described more specifically with reference to Examples. However, the following examples are only for illustrative purposes and are not intended to limit the scope of the invention.

Example 1

Research on Cytotoxicity of Pachastrissamine on HaCaT Cell Line and Malignant Melanoma Cell Line Pachastrissamine's cytotoxicity on a HaCaT cell line and a malignant melanoma cell line was researched through MTT cell viability analysis.

First, each of a HaCaT cell line (German Cancer Research, obtained from prof. N. Fuseni, Germany), and two kinds of malignant melanoma cell lines, B16F10 (B16) and A375 were inoculated into a DMEM (Dulbecco's Modified Eagle's Medium) culture medium added with 10% FBS (Thermo Fisher Scientific Inc.), 100 unit/ml penicillin, and 100 μg/ml streptomycin, and then cultured in a $CO_2$ incubator (Form a Scientific, Inc.) (37° C., 5%).

The cultured HaCaT, B16F10, and A375 cells were plated onto a 96-well plate at a concentration of $5 \times 10^4$ cells/well, and cultured in a $CO_2$ incubator (37° C., 5%) for 24 hours. The cells in respective wells were treated with pachastrissamine and phytosphingosine at various concentrations of 0, 0.9, 1.8, 3.7, 7.5, 10 μg/ml, and cultured in a $CO_2$ incubator (37° C., 5%) for 24 hours. After the culturing, in a state where the culture medium existed, each well was added with 5 mg/ml MTT reagent at a concentration of 20 μl/100 ml, and cultured in an incubator for 2 hours. After 2 hours, the culture medium was removed, and each well was added with 150 μl of DMSO (dimethyl sulfoxide). Then, a spectrophotometer was used to measure the absorbance at 540 nm, thereby analyzing the cell viability. Herein, the cell viability was represented as a relative value with respect to 100% of cell viability in a control group not treated with pachastrissamine and phytosphingosine.

Figure 1:
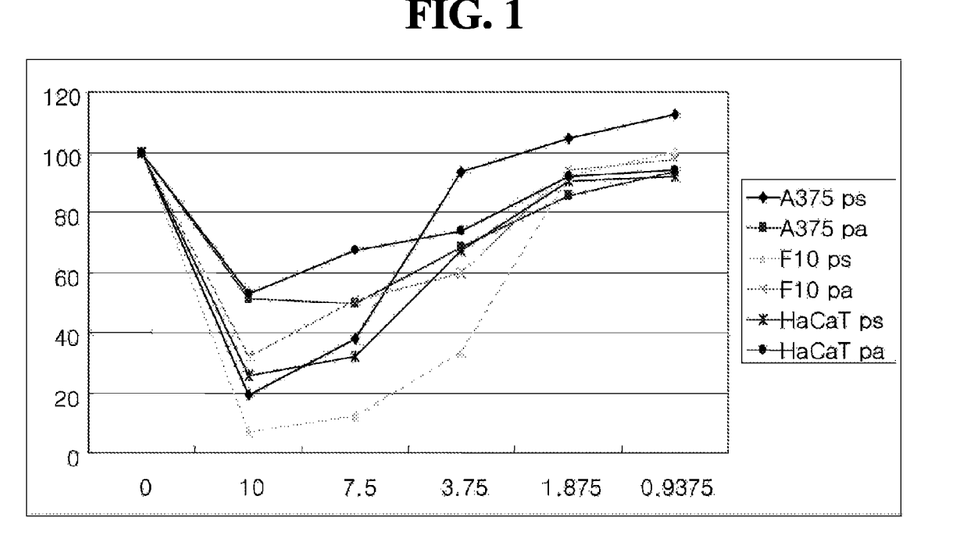
FIG. 1 shows the result of MTT analysis in an experiment on cytotoxicity of pachastrissamine and phytosphingosine.

As a result, it was found that as the concentration of pachastrissamine or phytosphingosine increased, the number of surviving cells was reduced. However, pachastrissamine showed a lower cytotoxicity than phytosphingosine (see FIG. 1).

Example 2

Research on Pachastrissamine's Effect on Cell Proliferation and Apoptosis

<2-1> Research on Pachastrissamine's Effect on Cell Proliferation

A HaCaT cell line was cultured in the same manner as described in Example 1. The cultured HaCaT cell line was plated onto a 60 mm plate at a concentration of $5 \times 10^4$ cells/well, and cultured in a $CO_2$ incubator (37° C., 5%) for 24 hours. The cultured cells in respective plates were treated with pachastrissamine at a concentration of 10 μg/ml, and cultured in a $CO_2$ incubator (37° C., 5%) for 24, 36, and 48 hours, respectively. After the culturing, the cells were washed with PBS, treated with trypsin-EDTA, and completely detached from the plate. Then, a hemocytometer was used to count the cells through trypan blue exclusion.

Figure 2:
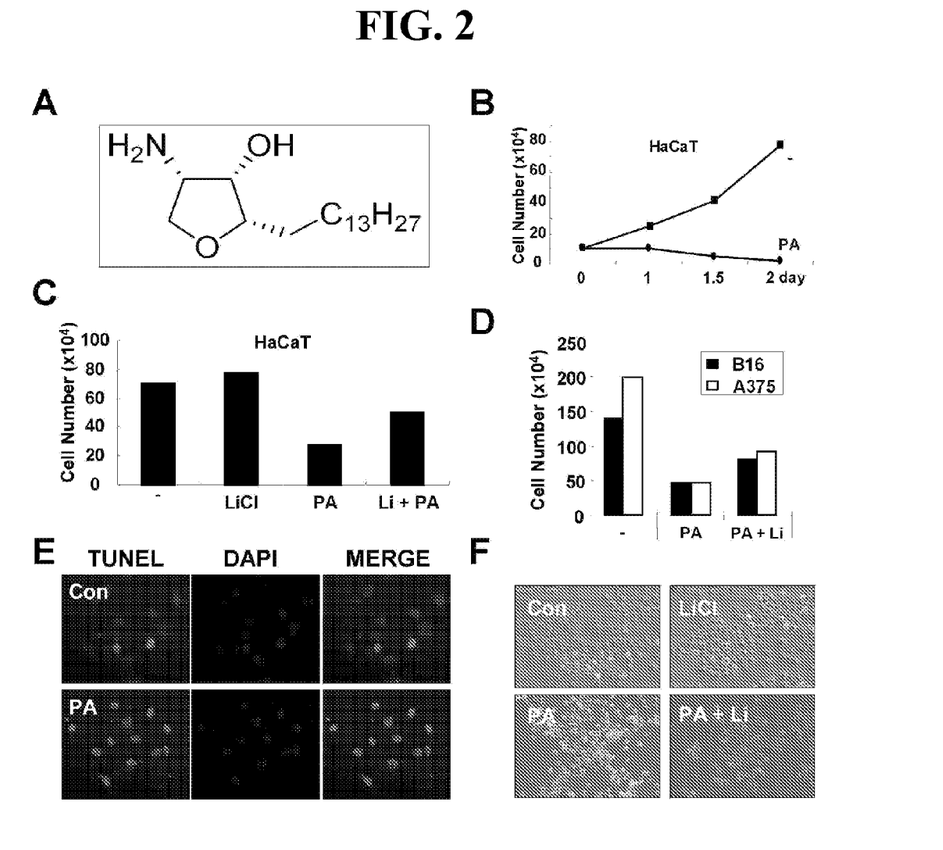
FIG. 2 shows the results of cell proliferation analysis and TUNEL analysis in an experiment on pachastrissamine's effect on cell proliferation inhibition and apoptosis promotion.

As a result, in the HaCaT cell line (control group) not treated with pachastrissamine, the number of cells increased, while in the HaCaT cell line treated with pachastrissamine, the number of cells decreased (see FIG. 2b). Accordingly, it was determined that pachastrissamine can inhibit cell proliferation.

<2-2> Research on Pachastrissamine's Effect on Induction of Apoptosis

HaCaT, B16F10 and A375 cell lines were cultured in the same manner as described in Example 1. The cultured HaCaT cell line was plated onto a 60 mm plate at a concentration of $5 \times 10^4$ cells/well, and cultured in a $CO_2$ incubator (37° C., 5%) for 24 hours. The cultured respective cells were divided into 4 groups. One group was added with only pachastrissamine (PA) at a concentration of 10 μg/ml; another group was added with lithium chloride (apoptosis inhibiting material) (at a final concentration of 300 nM) as well as pachastrissamine at a concentration of 10 μg/ml (PA+Li); and a third group was added with only lithium chloride (Li). The last group was a negative control group (Con) and was added with nothing. These groups were cultured in a CO2 incubator (37° C., 5%) for 24 hours, and then the number of cells were measured in the same manner as described in Example 2-2.

As a result, when HaCaT, B16F10 and A375 cell lines were treated with pachastrissamine, the number of cells was decreased as compared to a case in which pachastrissamine was not treated. When lithium chloride as well as pachastrissamine was treated, the number of cells was higher compared to a case in which only pachastrissamine was treated (see FIGS. 2C, and 2D). Accordingly, it was determined that pachastrissamine has an effect on the reduction of the number of cells, and is related to an apoptosis mechanism.

In order to determine if pachastrissamine induces apoptosis, TUNEL analysis and phase-contrast microscope observation were carried out.

The four groups of HaCaT cell samples were washed with PBS, and then surviving cells were subjected to morphology analysis through a phase-contrast microscope (see FIG. 2f).

As a result, like the measurement on the number of cells, when pachastrissamine was treated, the number of surviving cells was significantly reduced compared to a negative control group. Also, the cell division extent to be increased by lithium chloride (see FIG. 2D) was inhibited by treatment with pachastrissamine, and thus the number of surviving cells was reduced.

A HaCaT cell line was cultured in the same manner as described in Example 1. The cultured HaCaT cell line was plated onto a 60 mm plate at a concentration of $5 \times 10^4$ cells/well, and cultured in a $CO_2$ incubator (37° C., 5%) for 24 hours. The cultured cells were treated with pachastrissamine at a concentration of 10 μg/ml, cultured in a $CO_2$ incubator (37° C., 5%) for 24 hours, and subjected to TUNEL analysis.

In order to carry out TUNEL analysis based on ApopTag-Fluorescein In Situ Apoptosis Detection Kit (Millipore), cells were cultured in a cover slip, and washed with PBS (pH 7.4). In order to completely fix cells, the cells were reacted in a PBS solution including 4% paraformaldehyde at room temperature for 30 minutes. Then, in order to make the cells permeable, the cells were washed with a PBS solution, and reacted in a PBS solution including 0.1% Triton X-100 at room temperature for 5 minutes. For cell marking, the cells were washed with PBS twice, and then diluted TUNEL reaction mixture was added to the cover slip. After incubating in a humidified chamber at 37° C. for 60 minutes, the cover slip was washed. The washed cover slip was reacted with a DAPI solution at room temperature for about 10 minutes, washed with PBS, mounted on a slide, sufficiently dried in a dark place, and analyzed by a fluorescent microscope. A TUNEL positive nucleus was stained dark green, whereas the counter-stained nucleus was blue (see FIG. 2e).

As shown in FIG. 2E, as a result, in a negative control group (Con), only a limited part in observed cell nuclei (DAPI stained) showed apoptosis (TUNEL). On the other hand, when pachastrissamine was treated (PA), most of observed cell nuclei showed apoptosis. Accordingly, it was determined that pachastrissamine can significantly induce apoptosis.

Example 3

Research on Pachastrissamine's Cell Proliferation Inhibition Mechanism

<3-1> Research of Pachastrissamine's Effect on Control of AKT Activity

HaCaT, B16F10 and A375 cell lines were cultured in the same manner as described in Example 1. The cultured cells were plated onto a 6-well plate at a concentration of $3\times10^5$ cells/well, and cultured for 24 hours. After the culturing, after about 12 hours of serum starvation, the cells were treated with 10 µg/ml pachastrissamine and 5 µg/ml phytosphingosine. 30 minutes later, and 60 minutes later, each of the cell lines was resuspended in RIPA buffer [12 mM EDTA, 137 mM NaCl, 20 mM Tris-HCl (pH 8.0), 1 mM Na3VO4 (Sigma-Aldrich, USA) 10 mM NaF (Sigma), 1 mM PMSF (Sigma), 1% Triton X-100, 10% glycerol, protease inhibiting cocktail (Roche, Germany)], and then put on ice for 30 minutes so that the cells can be completely lysed. The lysate was centrifuged at 14000 rpm for 30 minutes, and the supernatant was collected. A BCA protein analysis kit (Pierce, Rockford, Ill.) was used to determine the concentration of each sample, and the sample was subjected to electrophoresis (SDS-PAGE). Western blotting was carried out on the protein isolated by the electrophoresis. After electrophoresis of the sample, the protein was transferred to a polyvinylidene fluoride membrane (Pall Corporation). Then, after blocking the membrane at room temperature for one hour using 5% BSA solution (Amresco, USA), it was treated with primary antibodies and reaction was carried out for 12 hours at 4° C. The primary antibodies were AKT antibody and Actin antibody (Cell Signaling Technology, Beverly, Mass.), which are antibodies associated in cell proliferation-related signaling. After reaction with primary antibodies, it was washed for about 30 minutes and further reacted for 1 hour at room temperature by treating with HRP-conjugated secondary antibodies. Then, after washing sufficiently for over 30 minutes, protein was identified using an ECL detection kit (intron Biotechnology).

Figure 3:
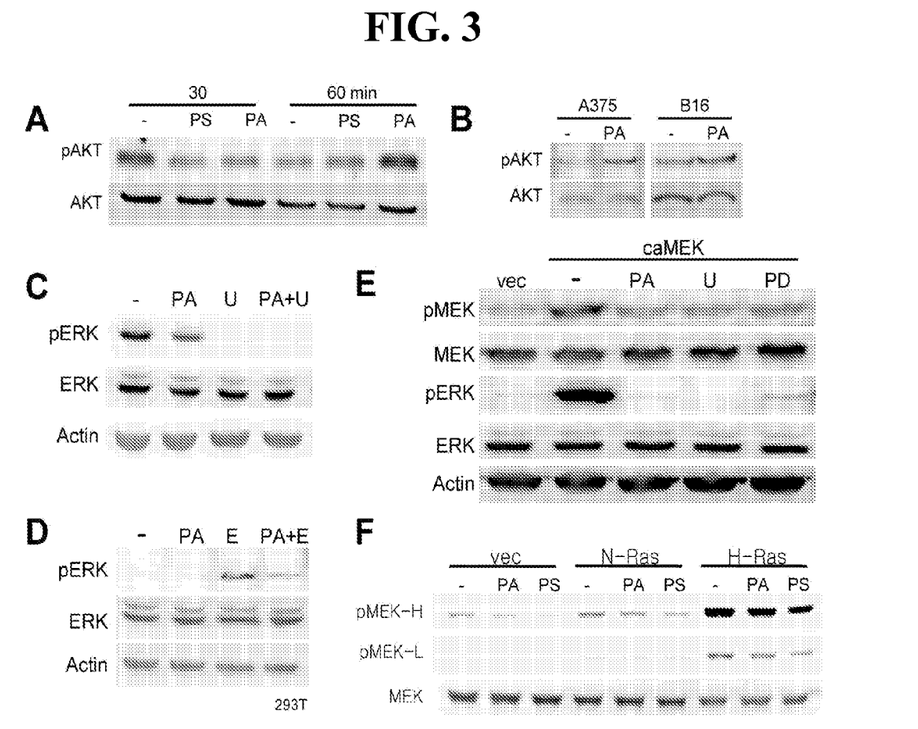
FIG. 3 shows the results of western blotting analysis in an experiment on pachastrissamine's apoptosis mechanism (pMEK-H:long-time exposure (90 s), pMEK-L:short-time exposure (30 s)

As a result, it was identified that in both the HaCaT cell line and the malignant melanoma cell line (B16F10, A375), after 30 minutes from the treatment with pachastrissamine and phytosphingosine, both samples showed a reduction of phosphorylation of AKT. However, after 60 minutes from the treatment, the degree of AKT phosphorylation in the sample treated with pachastrissamine was increased (see FIGS. 3A, and 3B).

<3-2> Research of Pachastrissamine's Effect on Control of ERK Activity

A HaCaT cell line was cultured in the same manner as described in Example 1. The cultured cells were divided into 4 groups, and plated onto a 6-well plate at a concentration of $3\times10^5$ cells/well, and cultured for 24 hours. After the culturing, after about 12 hours of serum starvation, one group was added with only pachastrissamine (PA) at a concentration of 10 µg/ml; another group was added with U0126 (ERK inhibitor, calbiochem technology) (at a final concentration of 20 nM) as well as pachastrissamine at a concentration of 10 µg/ml (PA+U); and a third group was added with only U0126 (U). The last group was a negative control group (−) and was added with nothing. These groups were reacted for 30 minutes, and then, in the same manner as described in Example 3-1, the cells were lysed, and western blotting was carried out using anti-pERK, anti-ERK and anti-actin antibodies so as to research activity of ERK protein (see FIG. 3C).

In the same manner, in a sample of HEK293T (Kidney epithelial cell) cell line treated with pachastrissamine and 100 µg/ml of EGF (epidermal growth factor), ERK activity was determined (see FIG. 3D).

In the same manner, MEK(caMEK) continuously activated in the HaCaT cell line was over-expressed so as to activate ERK in a lower signaling pathway of MEK. The HaCaT cell line whose ERK was activated by MEK was treated with pachastrissamine and U0126 and PD98059 (ERK inhibitors). Then, western blotting was carried out using anti-pMEK, anti-MEK, anti-pEKR, anti-EKR, and anti-actin antibodies so as to carry out comparative analysis (see FIG. 3E).

Further, in the same manner, two DNAs of N-Ras and H-Ras, in a previous step of MEK/ERK signal transduction, were over-expressed through transfection while a HaCaT cell line was cultured. Then, after treatment with pachastrissamine and phytosphingosine, western blotting was carried out using anti-pMEK, and anti-MEK antibodies so as to carry out comparative analysis of MEK activity (see FIG. 3F).

As a result, it was found that pachastrissamine has an effect on the reduction of ERK activation, and also can almost perfectly inhibit the ERK activity caused by EGF (see FIGS. 3C and 3D). Then, it was determined that pachastrissamine's effect on the inhibition of ERK activity was caused by an inhibition effect on MEK as an upper signal (see FIGS. 3E, and 3F). In conclusion, it was found that the cell proliferation inhibiting effect reported in Example 1 was caused by pachastrissamine's inhibition of MEK signal transduction related to ERK.

Example 4

Research on Pachastrissamine's Effect on the Expression Regulation of FoxO3a as a Cell Proliferation Inhibitor <4-1> Research on Pachastrissamine's Effect on the Expression Regulation of FoxO3a A HaCaT cell line was cultured in the same manner as described in Example 1. The cultured cells were plated onto a 6-well plate at a concentration of $3\times10^5$ cells/well, and cultured for 24 hours. After the culturing, after about 12 hours of serum starvation, the HaCaT cell line was treated with pachastrissamine and phytosphingosine in amounts of 5 and 10 µg/ml, for 24 hours. The cell line was lysed in the same manner as described in Example 3-1, and subjected to quantitative analysis. Then, western blotting was carried out by using FoxO3a antibody as a primary antibody.

Figure 4:
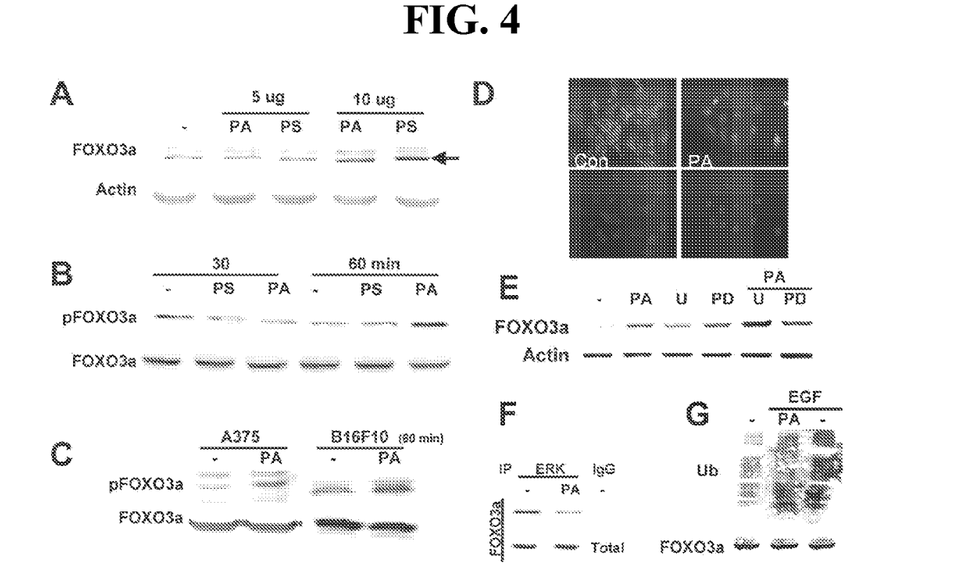
FIG. 4 shows the results of western blotting and Immunoprecipitation in an experiment on pachastrissamine's expression regulation of FoxO3a protein.

As a result, it was found that compared to a control group, in both samples treated with pachastrissamine and phytosphingosine, the extent of protein expression level of FoxO3a was increased (see FIG. 4A).

<4-2> Research on Pachastrissamine's Effect on the Expression of pFoxO3a

In the same manner as described in Example 4-1, a HaCaT cell line and malignant melanoma cell lines (A375 and B16F10) were treated with pachastrissamine and phytosphingosine at a concentration of 10 µg/ml for 30 minutes and 60 minutes, respectively. Then, western blotting was carried out using p-FoxO3a (Ser 253) antibody.

As a result, in a sample treated for 30 minutes, the amount of expressed p-FoxO3a was reduced with both drugs. On the other hand, in a sample treated for 60 minutes, unlike phytosphingosine, treatment with pachastrissamine increased an expression of p-FoxO3a (see FIGS. 4B and 4C).

<4-3> Research on Relationship Between Pachastrissamine's FoxO3a Expression Regulation Mechanism and AKT Pathway In order to carry out Immunocytochemistry analysis, cells were transferred to chamber slides, and cultured in a $CO_2$ incubator (37° C., 5%) for 24 hours. After about 12 hours of serum starvation, the cultured cell lines were treated with 10 μg/ml of pachastrissamine for 24 hours. The cell lines treated with pachastrissamine were fixed with 100% methanol, and washed with PBS. Then, in order to make the cells permeable, the cell lines were reacted in a 0.5% Triton X-100 and washed with a PBS solution. Then, by using a solution including 10% FBS and 0.1% gelatin, blocking was carried out at room temperature for 1 hour, and FoxO3a antibody was reacted at 4° C. for 12 hours. After the reaction, the cells were washed with PBS, reacted with a secondary antibody of Alex488 (invitrogen) at room temperature, and washed with PBS again. Finally, for nuclear stain, the cells were reacted with DAPI and washed with PBS. The slide was washed with PBS, attached with glass coverslip, and analyzed through a microscope.

As a result, when ser253 residue of FoxO3a is phosphorylated by AKT, FoxO3a is generally transported from a nucleus to a cytosol (liquid part of cytoplasm). In a sample treated with pachastrissamine, even though expression of p-FoxO3a was increased, the movement of FoxO3a protein to a nucleus was significantly increased as shown in FIG. 4D. From this result, it can be found that FoxO3a regulated by pachastrissamine acts independently from AKT, unlike phytosphingosine.

<4-4> Research on Erk Activity's (Inhibited by Pachastrissamine) Effect on FoxO3a Protein Expression Level As found in Example 3, pachastrissamine regulates ERK as well as AKT, and thus ERK pathway's effect on the regulation of FoxO3a expression was researched.

In the same manner as described in Example 3-2, a HaCaT cell line was treated with pachastrissamine, U0126, and PD98059, and in the same manner as described in Example 3-1, the cells were lysed. Then, western blotting was carried out by using FoxO3a antibody as a primary antibody so as to carry out comparative analysis on the level of protein expression.

As a result, in a sample treated with U0126 and PD98059, the level of protein expression of FoxO3a was significantly increased. Meanwhile, in a sample treated with pachastrissamine and U0126, the extent of protein expression of FoxO3a was significantly increased compared to other samples treated with each single material. However, in a sample treated with pachastrissamine and PD98059, it was not found that the extent of protein expression was increased compared to other samples treated with each single material (see FIG. 4E), because PD98059 has a significantly low affinity unlike ERK U0126.

In the same manner, a HaCaT cell line was treated with pachastrissamine, and immunoprecipitation was used to determine the degree of binding between ERK and FoxO3a, and the degree of FoxO3a ubiquitination caused by interaction. In order to carry out immunoprecipitation, the cells were plated on a 100 mm plate, and cultured in a $CO_2$ incubator (37° C., 5%) for 24 hours. After about 12 hours of serum starvation, the cultured cell line was treated with 10 μg/ml of pachastrissamine for 24 hours. The cell line treated with pachastrissamine and another cell line not treated with pachastrissamine were resuspended in the RIPA buffer as described above, and then put on ice for 30 minutes so that the cells could be completely lysed. The lysate was centrifuged at 14000 rpm for 30 minutes, and the supernatant was collected. A BCA protein analysis kit (Pierce, Rockford, Ill.) was used to determine the concentration of each sample, and the samples in the same amount were added with anti-ERK antibody in the same amount, and reacted at 4° C. for 2 hours. Then, each of the samples was added with 10 μl of protein G-agarose (GenDEPOT) and reacted at 4° C. for 10 hours, and then centrifuged at 3000 rpm for 1 minute, washed with RIPA buffer, and centrifuged again. Then, the precipitated protein G-agarose was collected, and electrophoresis was carried out.

As a result, in the sample treated with pachastrissamine, the degree of binding between ERK and FoxO3a was significantly decreased because the phosphorylation of ERK was inhibited by pachastrissamine, as shown in FIG. 3 or 4, thereby reducing the activity of ERK protein (see FIG. 4F).

In order to determine the degree of protein degradation of FoxO3a by interaction between ERK and FoxO3a, in the same manner as described in Example 3-2, HEK293T (Kidney epithelial cell) cell line was treated with pachastrissamine and EGF, and then the cells were lysed in the same manner as described in Example 3-1. Then, immunoprecipitation was carried out using FoxO3a antibody. The sample obtained from immunoprecipitation was subjected to western blotting by using ubiquitin antibody so as to carry out comparative analysis.

As a result, the ubiquitination degree increased by EGF was decreased by treatment with pachastrissamine. Accordingly, it was determined that the degradation of FoxO3a protein by ERK was inhibited by pachastrissamine, and pachastrissamine inhibited degradation of FoxO3a, thereby promoting FoxO3a's movement to a nucleus. In other words, pachastrissamine inhibited proliferation of cells and increased apoptosis.

From the results of Examples 4-1 to 4-4, it can be found that pachastrissamine or phytosphingosine stabilized protein of FoxO3a or increased the expression level of the protein. However, unlike phytosphingosine, in a cell line sample treated with pachastrissamine, the phosphorylation degree of AKT was not decreased but increased, because as described in Example 1, pachastrissamine has a lower cytotoxicity than phytosphingosine.

Example 5

Research on Pachastrissamine's Effect on FoxO3a Protein Degradation Induced by Beta-Catenin <5-1> Research on Pachastrissamine's Effect on Protein Expression Regulation by Beta-Catenin The pachastrissamine's effect on beta-catenin protein expression was researched. In the same manner as described in Example 1, a HaCaT cell line was cultured. The cultured cells were plated onto a 6-well plate at a concentration of $3 \times 10^5$ cells/well, and cultured for 24 hours. After the culturing, after about 12 hours of serum starvation, the cells were added with each of pachastrissamine (10 μg/ml) and lithium chloride (LiCl) (an inhibitor of GSK3-beta, GSK3-beta=beta-catenin inhibiting protein), at a final concentration of 300 nM, and reacted for 30 minutes. Then, the cells were lysed in the same manner as described in Example 3-1, and then western blotting was carried out using anti-pGSK3-beta, anti-GSK3-beta, anti-pCatenin and anti-Catenin antibodies so as to measure the amount of each protein.

Figure 5:
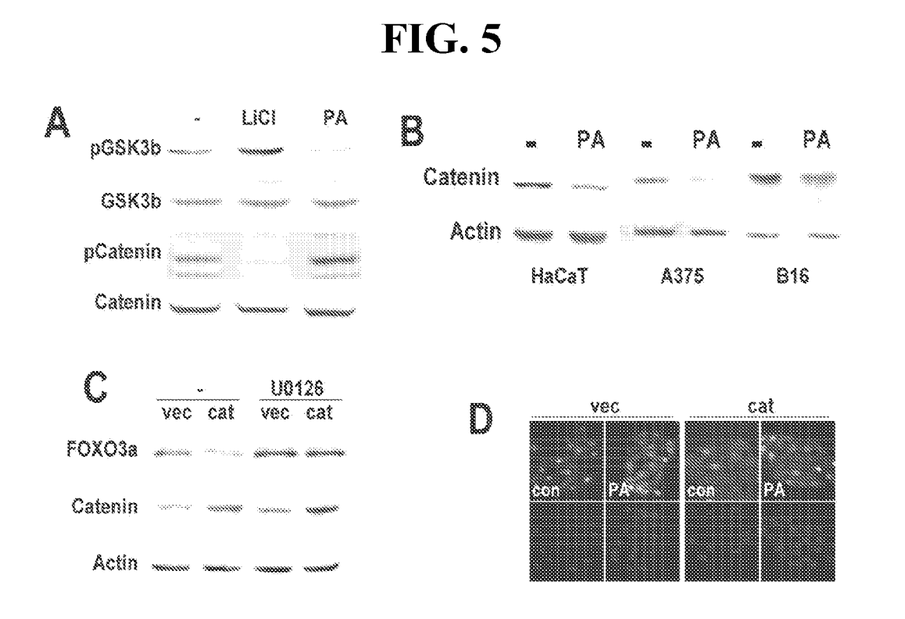
FIG. 5 shows the results of western blotting and cytochemistry in an experiment on pachastrissamine's effect on FoxO3a degradation induced by beta-catenin.
Figure 6:
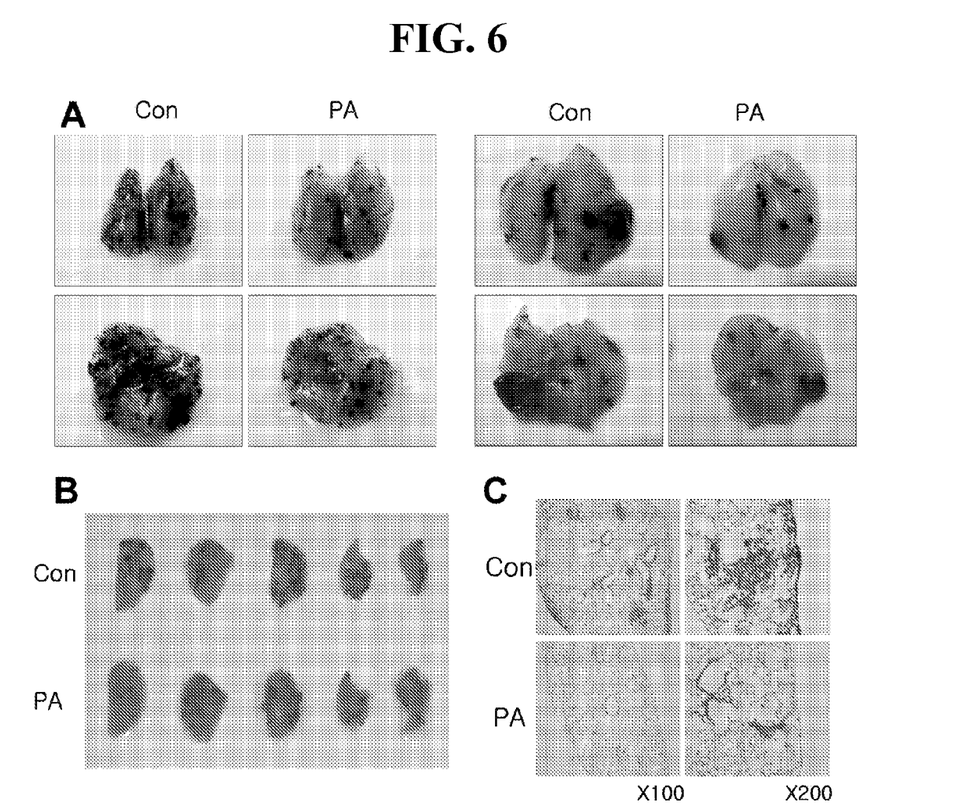
FIG. 6 shows the results of analysis on pachastrissamine's effect on the production of melanoma in a Lung Metastasis model.

As a result, when the cells were treated with LiCl, GSK3-beta was phosphorylated, thereby inhibiting protein activity. This inhibited the phosphorylation of beta-catenin, thereby stabilizing beta-catenin protein. On the other hand, the treatment with pachastrissamine resulted in the completely contrary effect to LiCl (see FIG. 5A). In other words, pachastrissamine induced the degradation of beta-catenin protein, thereby inhibiting cell proliferation.

From the above described result, it was determined that in a malignant melanoma cell line, pachastrissamine can induce the degradation of beta-catenin protein (see FIG. 5B).

<5-2> Research on Pachastrissamine's Effect on FoxO3a Protein Degradation Induced by Beta-Catenin In a HaCaT cell line, pachastrissamine's effect on FoxO3a protein which can be degraded over-expression of beta-catenin was researched. In the same manner as described in Example 1, the HaCaT cell line was cultured. The cultured cells were transfected with beta-catenin so as to induce over-expression of beta-catenin. The cultured cells were plated onto a 6-well plate at a concentration of $3\times10^5$ cells/well and cultured for 24 hours. After the culturing, after about 12 hours of serum starvation, cells with over-expression of beta-catenin and other cells with transfection of vector were treated with U0126 (ERK inhibitor), and reacted for 30 minutes. Then, in the same manner as described in Example 3-1, the cells were lysed, and western blotting was carried out so as to measure the amounts of FoxO3a and Catenin.

As a result, it was found that the expression level of FoxO3a protein was reduced by over-expression of beta-catenin. However, it can be found that in the sample treated with U0126, the reduced level of FoxO3a was restored. Also, in both samples with or without over-expression of beta-catenin, U0126 had no effect on the protein expression level of beta-catenin. Accordingly, it was determined that beta-catenin exists in the upper level than ERK signal (see FIG. 5C).

After the cells with or without over-expression of beta-catenin were treated with pachastrissamine, the distribution of intracellular FoxO3a protein was determined in the same manner as described in Example 4-3.

As a result, in the cell line sample with over-expression of beta-catenin, most of FoxO3a protein existed in cytosol outside the nucleus. Then, when the sample was treated with pachastrissamine, most of FoxO3a protein existing in cytosol moved into the nucleus again (see FIG. 5D).

Example 6

Research on Pachastrissamine's Effect on Malignant Melanoma Metastasis Inhibition in a Mouse Malignant Melanoma Metastasis Model In a C57BL6 mouse, pachastrissamine's effect on malignant melanoma metastasis inhibition was researched. A mouse (aged 6 weeks) was inoculated with a malignant melanoma cell line B16F10 ($1\times10^6$) through a tail vein. After 24 hours from the inoculation, pachastrissamine was inoculated, and also, in a control group, PBS was inoculated in the same amount. Pachastrissamine was inoculated once per 4 days (three times), and on the 14th day from the inoculation of cells, the mouse was dissected to extract the lung. The extracted lung was immersed in 4% formalin solution for 16 hours or more, and washed for 16 hours or more. After the washing, the extracted lung was photographed, and other tissues were embedded in paraffin to make a block. Then, a tissue slice with a thickness of 5 μg was prepared. The tissue slice was subjected to a deparaffin process for H&E (Hematoxylin & Eosin) staining, and then sequentially reacted with 100%, 90%, 80%, 70%, and 60% alcohol solutions to complete the hydration reaction. The completely hydrated slice was subjected to H&E staining, and then reacted with the alcohol solutions in reverse order of the hydration reaction to perform a dehydration reaction. When the dehydration reaction was completed, the slice was fixed on a slide and observed by a microscope.

As a result, it was found that in the mouse inoculated with pachastrissamine, the malignant melanoma metastasis to the lung was significantly inhibited compared to that in a control group. Accordingly, it was determined in the malignant melanoma metastasis experiment using a mouse, pachastrissamine has an excellent effect on metastasis inhibition.

As described above, the inventive pharmaceutical composition for preventing or treating hyper-proliferative skin diseases comprises pachastrissamine or a pharmaceutically acceptable salt thereof as an active ingredient. The pachastrissamine inhibits the degradation of FoxO3a protein and increases the expression of FoxO3a protein. Thus, the inventive pharmaceutical composition induces apoptosis of hyper-proliferative cells and is effective in apoptosis in skin cancer such as malignant melanoma. Accordingly, the inventive pharmaceutical composition comprising pachastrissamine or a pharmaceutically acceptable salt thereof as an active ingredient can be used for preparing agents for treating and preventing hyper-proliferative skin diseases such as skin cancer, and psoriasis.

The foregoing descriptions of specific exemplary embodiments of the present invention have been presented for purposes of illustration and description. They are not intended to be exhaustive or to limit the invention to the precise forms disclosed, and obviously many modifications and variations are possible in light of the above teachings. The exemplary embodiments were chosen and described in order to explain certain principles of the invention and their practical application, to thereby enable others skilled in the art to make and utilize various exemplary embodiments of the present invention, as well as various alternatives and modifications thereof. It is intended that the scope of the invention be defined by the Claims appended hereto and their equivalents.

The invention claimed is:

1. A method for treating a hyper-proliferative skin disease comprising administering an effective amount of pachastrissamine represented by the Chemical Formula 1 or a pharmaceutically acceptable salt thereof to a subject in need thereof, wherein the hyper-proliferative skin disease is selected from the group consisting of psoriasis, ichthyosis, solar keratosis, Bowen's disease, papilloma, eczema, addictive eczema, atopic dermatitis, acne vulgaris, seborrheic dermatitis, lichen planus, lichen planus striatus, foot hyperkeratosis, seborrheic keratosis, actinic keratosis, cutaneous wart lesion, skin aging, and photoaging,

[Chemical Formula 1]

2. A method for inhibiting metastasis of a skin melanoma cell comprising administering an effective amount of pachastrissamine represented by Chemical Formula 1 or a pharmaceutically acceptable salt thereof to a subject in need thereof,

[Chemical Formula 1]

* * * * *